United States Patent [19]

Chapman, II

[11] 4,410,381

[45] Oct. 18, 1983

[54] METHODS AND APPARATUS FOR TESTING THE QUALITY OF AN ULTRASONIC WELD IN THERMOPLASTIC MATERIAL

[75] Inventor: Gilbert B. Chapman, II, Southfield, Mich.

[73] Assignee: Ford Motor Company, Dearborn, Mich.

[21] Appl. No.: 342,971

[22] Filed: Jan. 26, 1982

[51] Int. Cl.³ .............................................. G05G 15/00
[52] U.S. Cl. ...................................... 156/64; 156/73.1; 156/378; 156/580.1; 250/338
[58] Field of Search ............. 156/73.1, 73.2, 580.1, 156/580.2, 359, 64, 378; 250/338, 339, 358 R; 53/507, 508, 75

[56] References Cited

U.S. PATENT DOCUMENTS

| | | | |
|---|---|---|---|
| 2,915,638 | 12/1959 | Poole | 250/83.3 |
| 3,158,928 | 12/1964 | Prisco et al. | 29/470.1 |
| 3,191,441 | 6/1965 | Erickson | 73/432 |
| 3,245,261 | 4/1966 | Buteux et al. | 73/355 |
| 3,494,816 | 2/1970 | Fener | 156/359 |
| 3,734,382 | 5/1973 | Spanjer | 228/1 |
| 3,791,569 | 2/1974 | Mims | 228/1 |
| 3,827,619 | 8/1974 | Cusick et al. | 228/1 |
| 3,868,508 | 2/1975 | Lloyd | 250/330 |
| 3,908,886 | 9/1975 | Raske | 228/1 |
| 3,930,159 | 12/1975 | Marquet | 250/338 |
| 4,040,885 | 8/1977 | Hight et al. | 156/378 |
| 4,047,657 | 9/1977 | Mims | 228/103 |
| 4,168,430 | 9/1979 | Denis et al. | 250/338 |
| 4,214,164 | 7/1980 | Traub et al. | 250/338 |

*Primary Examiner*—David A. Simmons
*Attorney, Agent, or Firm*—Paul K. Godwin, Jr.; Robert D. Sanborn

[57] ABSTRACT

Ultrasonically welded thermoplastic materials are non-destructively inspected by sensing the infrared radiation emitted from the weld region of the material during or immediately subsequent to the welding operation. The sensed radiation levels are compared with a predetermined value and if they exceed the predetermined value are indicative of an acceptable weld. If the sensed radiation peak does not exceed the predetermined level, the weld is deemed to be unacceptable.

7 Claims, 4 Drawing Figures

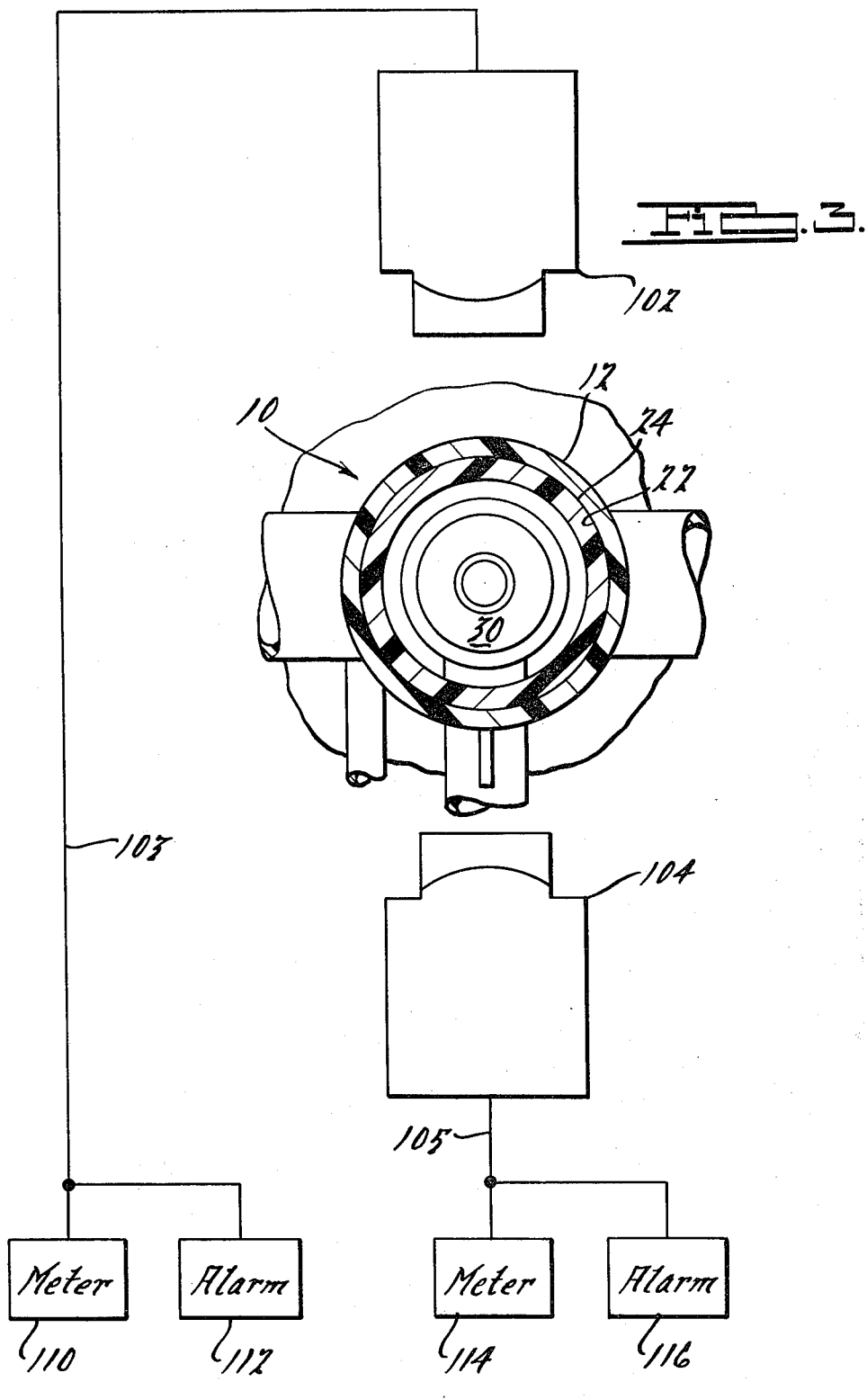

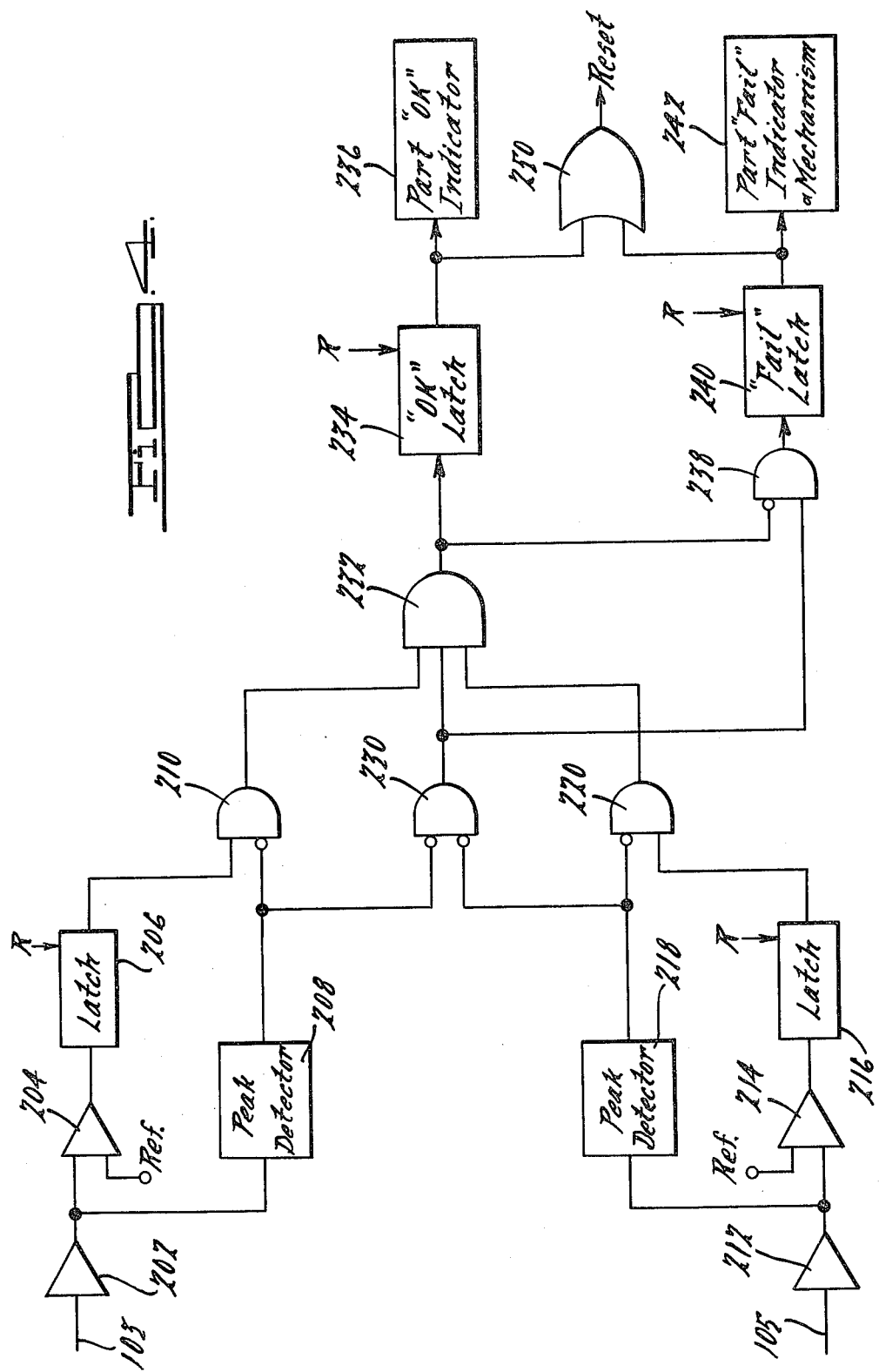

METHODS AND APPARATUS FOR TESTING THE QUALITY OF AN ULTRASONIC WELD IN THERMOPLASTIC MATERIAL

BACKGROUND OF THE INVENTION

1. Field of the Invention

The present invention is directed to the field of nondestructive testing and more particularly to the area of inspecting ultrasonic welds in thermoplastic material.

2. Description of the Prior Art

During the formation of parts from thermoplastic materials, it is common to join separate pieces by utilizing ultrasonic welding processes. However, the common forms of evaluating the quality of the weld employ destructive testing techniques. Pressure or pull tests are employed which determine the fracture point of the weld. Due to the nature of any destructive test, statistical sampling techniques are necessitated, since each tested part is destroyed.

While the use of ultrasonic welds and statistical samplings have, in general, provided manufacturers with a predictable yield rate, it is more desirable to provide an automatic nondestructive technique whereby 100% inspection can be made of the ultrasonic weld in thermoplastic material to thereby provide a quality sort of the welded parts.

SUMMARY OF THE INVENTION

The inventor's analysis of ultrasonic weld failures in thermoplastic parts identified several instances where inferior welds may result.

One of those instances occurs when parts are not precisely positioned, due to the parts positioning equipment or due to the design of the parts themselves. When ultrasonic vibrations are applied to misaligned parts, they will fuse only at the abutting surfaces. Consequently, some points become welded and some do not.

Another of those instances occurs when the parts are formed from different composition batches, wherein small differences in composition may result in different melting points. In some instances, one part will melt while the other remains solid during the application of ultrasonic vibrations, thereby producing a poor weld.

Yet another instance of inferior weld may occur when weld parameters, such as weld power, hold time and weld hold down pressure drift from their preset values. The present invention provides for nondestructive inspection to determine ultrasonic weld quality in thermoplastic materials and is easily adapted to provide 100% inspection of welded parts during the manufacture. The present invention involves the monitoring of infrared radiation emitted from the surface adjacent the weld region, as a result of an ultrasonic weld being performed thereon. A properly welded region will reach a predetermined fusing temperature for the particular thermoplastic material. By utilizing destructive test methods, it has been determined that the strength of the welds are directly related to the maximum temperature reached during the welding operation. Therefore, standards are derived for the minimal temperature that must be reached before an acceptable weld is made.

The present invention monitors the infrared radiation emitted from an ultrasonically welded thermoplastic material. When the monitored radiation reaches an intensity above that for which an acceptable weld has been determined to have been made, the weld is deemed to be satisfactory. If, however, the intensity of the emitted radiation does not reach the predetermined level, the weld is deemed to be unsatisfactory and the part is rejected or analyzed to determine the reasons for the failure. Consequently, the present invention is ideally suited for instantaneous process failure analysis and 100% testing of the mechanically induced welds.

It is an object of the present invention to provide an on-line nondestructive method and apparatus for evaluating the quality of ultrasonically performed welds on thermoplastic material.

It is another object of the present invention to provide means by which instantaneous process failure analysis may be performed, in order to effect higher yield in ultrasonically welded thermoplastic parts.

BRIEF DESCRIPTION OF THE DRAWINGS

FIG. 3 is a top view of the inspection station of FIG. 2, showing a cross-section of the welded part and associated monitoring devices.

FIG. 4 is a schematic block diagram of an evaluation circuit as may be utilized in the present invention.

DETAILED DESCRIPTION OF THE PREFERRED EMBODIMENT

Figure 1:
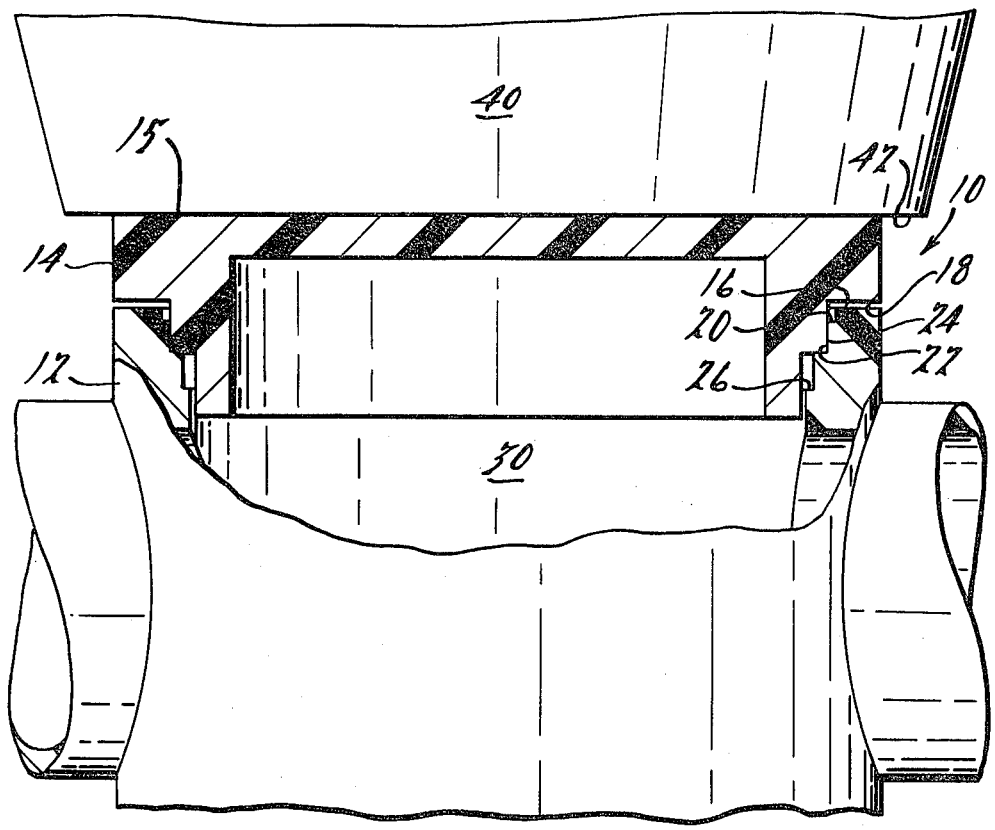
FIG. 1 is an elevational cross-section of a typical part being subjected to ultrasonic welding.

A thermoplastic part 10 is shown in FIG. 1 in position to be ultrasonically welded. The support base 12, in this case, is a cylindrically formed valve body of thermoplastic material. The base 12 defines a central cavity 30 and contains an upper opening defined by an annular surface 16. A cap piece 14 is formed of the same thermoplastic material to fit inside the base 12 and contains a cylindrical outer surface 24 that abuts an internal cylindrical wall 22 of the base 12.

When mechanical stress waves are applied to the upper surface 15 of the cap piece 14 via a pressure contact through surface 42 of an ultrasonic transducer 40, the abutting surfaces 22 and 24 are caused to fuse and form a weld region. The mechanical vibrations cause solid surfaces 22 and 24 to produce sufficient frictional heat that the thermoplastic surfaces melt. If both surfaces melt at the same temperature, as they should, some of the melt escapes into adjacent flashing zones 20 and 26 and the region becomes fused. If, on the other hand, the surfaces are not abutting or one material melts prior to the other, the temperature of the region will not reach the known fusing temperature.

The present invention evaluates the weld by monitoring the amount of heat radiated from the weld region immediately subsequent to the welding operation. Weld and inspection zones A and B are respectively shown in FIG. 2 as a production embodiment for the present invention. In that embodiment, the part 10 is loosely assembled prior to being conveyed to weld zone A. When conveyed to the weld zone A, the ultrasonic transducer 40 make a pressure contact with the part and applies ultrasonic vibrations to the part for a predetermined period of time. Subsequently, the part 10 is conveyed to an inspection zone B where a plurality of sensors 102 and 104 are positioned to receive infrared radiation emitted from the weld region. The sensors 102 and 104 are, in this embodiment, Capintec/Heimann S-1548 infrared thermometers with a spectral range of 8–14 microns. It is foreseeable that a greater number of sensors could be installed along the entire length of the weld region to increase the resolution of the inspection. In this embodiment, however, the use of two diametrically opposed sensors was found to be adequate to detect the incomplete welds that cause part failures for the particular part shown.

Figure 2:
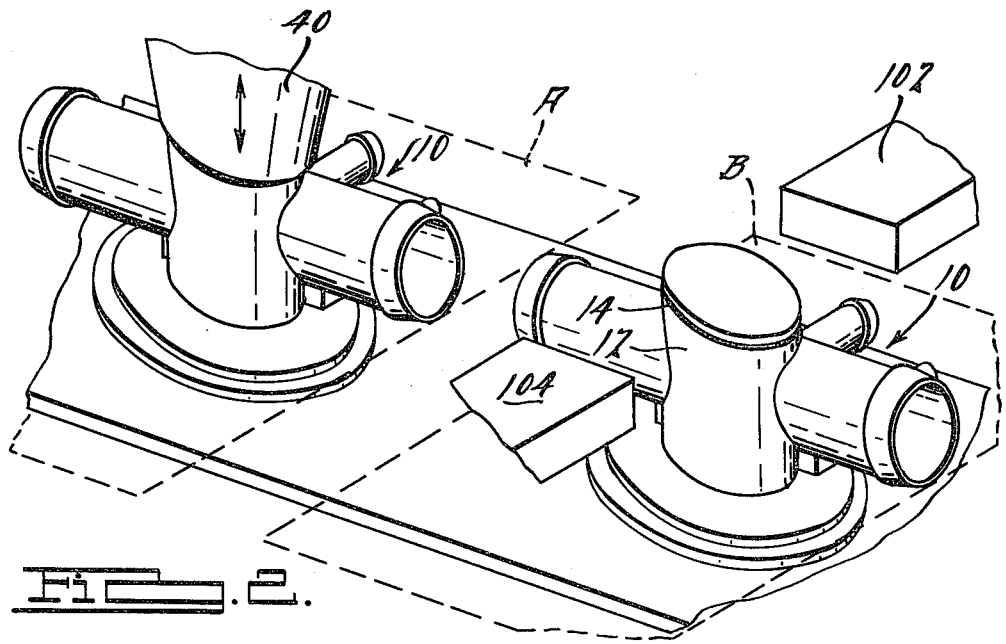
FIG. 2 is a perspective view of welding and inspection stations incorporating the present invention.

A top cross-sectional view of the FIG. 2 embodiment is shown in FIG. 3 and the sensors are shown connected to meter and alarm devices. In the cross-sectional view of the part 10, the weld joint formed by the abutting surfaces 22 and 24 is shown as cylindrically encompassing the central cavity 30 of the part 10. The heat produced at the weld region is conducted through the base 12 and emitted at the outer surface of the part 10. The sensors 102 and 104 are located so as to receive a narrow band of frequencies in the infrared range and produce output signals on respective lines 103 and 105 indicative of the intensity of the received radiation. The sensor 102 is connected to a meter 110 and a preset alarm 112 through signal line 103. Similarly, the sensor 104 is connected to a meter 114 and a preset alarm 116 through signal line 105. Of course, the meters 110 and 114 are merely for monitoring purposes while the alarms 112 and 116 symbolize a more elaborate circuit by which the part may be automatically discarded or otherwise marked to indicate a problem resulting in substandard assembly and welding operations for that part.

A more detailed block diagram for the alarm system is shown in FIG. 4, wherein the outputs from the individual infrared sensors are respectively compared with a known reference value which corresponds to the predetermined fusing temperature that must be reached in order to effect an acceptable weld. If any one of the sensors fails to receive radiation from the welded part of a sufficient intensity to indicate an acceptable weld, a "FAIL" indicator is activated along with a mechanism for separating inferiorly welded parts away from the acceptable parts.

The FIG. 4 circuit incorporates separate monitoring features for each signal channel from respective sensors wherein the signal value from each sensor is separately compared with a predetermined reference until such time as the signal value starts to decrease. Such a decrease in signal value indicates that the intensity of the infrared radiation has reached its peak and is on the decline. The results of each comparison are stored and appropriately gated through a logic network to determine the acceptability or unacceptability of the welded part. Specifically, signal line 103 is connected to a buffer amplifier 202. The output of the buffer amplifier 202 is connected to one of the inputs of a comparator circuit 204. The other input is connected to a reference voltage source which is preselected in value to correspond to a minimum signal level attributed to intensity of radiation that the sensors should receive from an acceptable weld. The output of the comparator circuit 204 is normally at a low level until such time as the output from the buffer amplifier 202 exceeds the reference voltage value. At that time, the output of the comparator circuit 204 switches to a high level signal that is stored in a latch 206. The high level signal stored in the latch 206 is communicated to an input terminal of an AND gate 210.

A peak detector circuit 208 has its input connected to the output of buffer amplifier 202 parallel to the input to the comparator 204. The peak detector circuit 208 provides a high level output signal as long as the signal value output from the amplifier 202 is increasing. When the signal level output value from the amplifier 202 reaches its peak and starts to decrease in value, the output from the peak detector 208 switches to a low level signal. The output from the peak detector circuit 208 is fed to an inverting input terminal of the AND gate 210 so that a high level signal will be output therefrom only when the signal value from the amplifier 202 has exceeded the reference voltage value and the signal from the amplifier 202 has been determined to have reached its peak.

Similar analysis is made to the signal input on line 105 through buffer amplifier 212, a comparator circuit 214, a latch 216 and a peak detector circuit 218. The outputs of the peak detector circuit 218 and the latch 216 are fed to an AND gate 220 that has its output connected to an input of AND gate 232.

In order to determine that the radiation received has reached its highest level in each of the monitoring circuits, an AND gate 230 has inverting input terminals connected to receive the outputs of the peak detector circuits 208 and 218. The output of AND gate 230 then enables the AND gate 232 to provide a high level output only if the radiation received by each sensor has reached the acceptable level. In the event that any of highest signal values measured in any of the channels is less than the predetermined reference value, the output of AND gate 232 will be at a low level.

The output of the AND gate 232 is connected to an "O.K." latch 234 that is in turn connected to a "PART O.K." indicator 236 to provide an evaluation of the welded part. The output of the AND gate 232 is also connected to an inverting input terminal on an AND gate 238. Another input terminal of the AND gate 238 is connected to receive the output of AND gate 230. When all the signal values have been compared, the output of the AND gate 230 provides an enabling signal to both AND gate 238 and AND gate 232. if the output of AND gate 232 is at a low level, and the output of AND gate 238 is at a high level, the high level signal is stored in a "FAIL" latch 240. The output of the "FAIL" latch 240 is fed to a "PART FAIL" indicator and mechanism 242, which may include a buzzer, a light or some other warning device and a conventional conveyor diversion mechanism to separate the failed part from the accepted parts.

An OR gate 250 has its input terminals respectively connected to the outputs of the latch 234 and latch 240 and responsively provides a reset signal to each of the latches 206, 216, 234 and 240 thereby conditioning the circuit to evaluate the next part positioned for inspection.

While it is apparent that many modifications and variations may be made without departing from the true spirit and scope of the invention, it is intended by the appended claims to include all such variations and modifications of the preferred embodiment.

I claim:

1. An apparatus for testing the quality of an ultrasonic weld in thermoplastic material comprising:
   means for sensing electromagnetic radiation within a predetermined range of wavelengths emitted from said welded material for a period of time immediately following said weld;
   means connected to said sensing means for responsively producing an output signal having values directly related to said sensed radiation; and means receiving said output signal for comparing the highest value thereof occuring during said period of time with a predetermined value corresponding to that of an acceptable weld and indicating whether said highest value is above or below said predetermined value.

2. An apparatus as in claim 1, in which said sensing means senses infrared radiation emitted within a predetermined band of wavelengths.

3. An apparatus as in claim 1, wherein said sensing means includes a plurality of infrared sensors spaced along said weld;
said responsive means responds to each sensor by providing output signals corresponding to respective sensors; and
said comparing means compares each output signal value with said predetermined value and said indicating means indicates if any of the highest values of said signals does not exceed said predetermined value.

4. A method of testing quality of an ultrasonic weld in a thermoplastic material comprising the steps of:
performing an ultrasonic weld on said material for a first predetermined time period;
sensing the intensity of electromagnetic radiation within a predetermined band of wavelengths, emitted from said welded material immediately following said weld step for a second period of time;
producing an output signal having values directly related to said sensed radiation intensity;
comparing the highest value of said output signal occuring during said second period of time with a predetermined value corresponding to that of an acceptable weld; and
indicating whether said highest value is above or below said predetermined value.

5. A method as in claim 4, wherein said step of sensing is performed to sense the intensity of infrared radiation emitted within a predetermined band of wavelengths.

6. A method as in claim 4, wherein said sensing step is performed at a plurality of points along said weld, said step of producing an output signal is performed for each point of sensing, said step of comparing is performed against each output signal produced and said indicating step is performed for each comparison.

7. A method as in claim 6, wherein said step of sensing is performed at said plurality of points by sensing the intensity of infrared radiation emitted within a predetermined band of wavelengths.

* * * * *